United States Patent [19]
Grollier et al.

[11] Patent Number: 5,192,544
[45] Date of Patent: * Mar. 9, 1993

[54] COSMETIC OR PHARMACEUTICAL COMPOSITION FOR TOPICAL APPLICATION CONTAINING AT LEAST ONE RETINOID DERIVATIVE AND AT LEAST ONE PYRIMIDINE DERIVATIVE, ITS USE AS A MEDICINAL PRODUCT AND CORRESPONDING TREATMENT PROCESS

[75] Inventors: Jean-François Grollier, Paris; Georges Rosenbaum, Asnieres; Isabelle Richoux, Paris, all of France

[73] Assignee: L'Oreal, Paris, France

[*] Notice: The portion of the term of this patent subsequent to Nov. 6, 2007 has been disclaimed.

[21] Appl. No.: 595,474

[22] Filed: Oct. 11, 1990

[30] Foreign Application Priority Data

Oct. 12, 1989 [FR] France .................. 89 13358

[51] Int. Cl.$^5$ .................. A61K 7/06; A61K 9/10; A61K 31/505; A61K 31/44
[52] U.S. Cl. .................. 424/401; 424/401; 424/450; 424/484; 424/489; 436/829; 514/256; 514/275; 514/777; 514/778; 514/779; 514/780; 514/781; 514/782; 514/880; 514/881; 514/963

[58] Field of Search .............. 424/401, 450, 484, 489; 436/829; 514/725, 777–782, 880, 881, 963, 256, 275

[56] References Cited

U.S. PATENT DOCUMENTS 4,857,525  8/1989  Philippe et al. ............. 514/554
4,968,685  11/1990  Grollier ....................... 514/256

FOREIGN PATENT DOCUMENTS 8807362  10/1988  PCT Int'l Appl. .
2189457  10/1987  United Kingdom .

Primary Examiner—Thurman K. Page
Assistant Examiner—Carlos Azpuru
Attorney, Agent, or Firm—Cushman, Darby & Cushman

[57] ABSTRACT

Cosmetic or pharmaceutical composition consisting of a dispersion in a physiologically acceptable aqueous phase D of vesicles of ionic and/or nonionic amphiphilic lipid(s), the vesicles being bounded by one or more lipid lamellae, the lipid lamellae containing at least one retinoid compound and the aqueous dispersion phase a pyrimidine derivative. The said composition may be used by topical application on the hair and scalp.

21 Claims, No Drawings

COSMETIC OR PHARMACEUTICAL COMPOSITION FOR TOPICAL APPLICATION CONTAINING AT LEAST ONE RETINOID DERIVATIVE AND AT LEAST ONE PYRIMIDINE DERIVATIVE, ITS USE AS A MEDICINAL PRODUCT AND CORRESPONDING TREATMENT PROCESS

The present invention relates to a composition containing, in combination, at least one retinoid derivative and at least one pyrimidine derivative, which is light-stable and stable on storage. This composition may be used as a medicinal product or as a cosmetic for inducing and stimulating hair growth and for decreasing its loss.

Man has a stock of 100,000 to 150,000 hairs, and it is normal to lose 50 to 100 hairs daily. The maintenance of this stock results essentially from the fact that the life of a hair is subjected to a hair cycle, during which the hair forms, grows and is shed before being replaced by a new hair which appears in the same follicle. During a hair cycle, three phases are observed successively, namely: the anagen phase, the catagen phase and the telogen phase. During the first, so-called anagen phase, the hair passes through a period of active growth associated with an intense metabolic activity in the bulb. The second, so-called catagen phase is transitional, and is marked by a slowing of mitotic activity. During this phase, the hair undergoes changes, the follicle atrophies and the level of its implantation in the skin is seen to be progressively raised. The terminal, so-called telogen phase corresponds to a rest period of the follicle, and the hair is finally shed, pushed by a nascent anagen hair. This process of permanent physical renewal undergoes a natural evolution in the course of ageing; the hairs become thinner and their cycles shorter. Alopecia occurs when this process of physical renewal is accelerated or disturbed, that is to say when the growth phases are shortened, the transition of the hairs to the telogen phase takes place sooner and the hairs are shed in larger number. Successive growth cycles lead to progressively thinner and progressively shorter hairs, gradually converting to an unpigmented down which can lead to baldness. The hair cycle is dependent, moreover, on many factors capable of bringing about a more or less pronounced alopecia. Among these factors, nutritional, endocrine and nervous factors may be mentioned.

Compositions enabling the effect of alopecia to be abolished or reduced, and in particular hair growth to be induced or stimulated and its loss decreased, have been sought for many years in the cosmetic or pharmaceutical industry. It is endeavoured, in particular, to prolong the anagen phase of the hair cycle relative to the telogen phase which, as described above, leads to hair loss. Certain pyrimidine derivatives, especially the derivative generally known as "minoxidil", are known to promote hair growth.

In Application WO-A-83/02,558, it has already been proposed to use retinoid derivatives, especially all-trans-retinoid acid or tretinoin, combined with minoxidil for hair treatment. The combination of these two products improves, relative to minoxidil alone, the rate of hair growth, prolongs the anagen phase of the hair cycle and enables some cases of alopecia to be treated. In these lotions for topical application, the retinoid, which is not water-soluble, is generally dissolved in ethyl alcohol or propylene glycol. Unfortunately, the presence of these solvents gives the lotion an irritant nature with respect to the skin. In addition, retinoids, and in particular all-trans-retinoic acid, display some degree of instability to light, and it has been found that the presence of minoxidil in all-trans-retinoic acid compositions accelerates the degradation of the retinoid caused by light and/or during storage.

To remedy the latter drawback, it has been proposed to store the retinoic derivative and the pyrimidine derivative separately, and to apply them separately in succession. However, this treatment is relatively complicated for the user, since it necessitates the use of two packs and applications at specified intervals.

The Applicant has now discovered a composition containing, in combination, a least one retinoid derivative and at least one pyrimidine derivative which may be stored without degradation of the retinoid derivative taking place. In addition, the composition has the advantage of being in an aqueous medium and of not containing solvents having an irritant nature with respect to the skin.

The subject of the present invention is a cosmetic or pharmaceutical composition for topical application containing, in combination, at least one retinoid derivative and at least one pyrimidine derivative, characterized in that it consists of a dispersion of vesicles of ionic or nonionic amphiphilic lipids, the vesicles being bounded by one or more lipid lamella(e) in a physiologically acceptable aqueous dispersion phase D, the retinoid derivative(s) being in the lipid lamellae of the vesicles whereas the pyrimidine derivative(s) is (or are) in the form of a solution or, partially or totally, in the form of a suspension in the aqueous phase D.

The composition according to the invention has the advantage of being light-stable. It is not necessary to store it in a tinted or completely opaque bottle. Moreover, it should be noted that the composition does not contain a solvent other than water: it is hence not irritant. On the contrary, the ionic or nonionic lipids forming the vesicles have a demulcent action with respect to the scalp. Furthermore, it permits optimal skin absorption and a good distribution of the active substances, with a gradual and controlled release of the active principles which provides for a prolonged action between two applications.

The vesicles of nonionic amphiphilic lipids and the vesicles of ionic lipids are, in a known manner, vesicles bounded by one or more bimolecular or multimolecular lipid lamellae encapsulating an aqueous phase E; they are dispersed in an aqueous dispersion phase D. The vesicles of ionic amphiphilic lipids are, for example, described in the paper by A. D. BANGHAM, published in J. Mol. Biol. (1965), 13, 238–252, and the vesicles of nonionic lipids in French Patent 2,315,991.

Among ionic lipids usable for obtaining vesicles, natural or synthetic phospholipids may be mentioned. It is possible, in particular, to use soybean lecithin or hydrogenated lecithin.

The nonionic lipids used for manufacture of the vesicles are advantageously selected from the group composed of the compounds of formula (I):

$$RO\text{–}[C_3H_5(OH)O]_{\overline{n}}H \tag{I}$$

where $\text{–}C_3H_5(OH)O\text{–}$ is represented by the following structures, taken mixed or separately:

$CH_2CHOHCH_2O-$;  $-CH_2CHO-$;  $-CH-CH_2O-$
                               |              |
                              $CH_2OH$       $CH_2OH$ where $\bar{n}$ is an average statistical value between 2 and 6;
where R is:

a) either an aliphatic chain $R_1$ or a residue $R_2CO$, $R_1$ being a linear or branched $C_{12}-C_{18}$ aliphatic radical and $R_2$ being a linear or branched $C_{11}-C_{17}$ aliphatic radical;

b) or $R_3 \pm O-C_2H_3(R_4)\exists$ where $-OC_2H_3(R_4)-$ is represented by the following structures, taken mixed or separately:

$-O-CH-CH_2-$  and  $-O-CH_2-CH-$;
    |                        |
    $R_4$                    $R_4$ $R_3$ being a radical $R_1$ or $R_2CO$ and $R_4$ being a radical $R_1$, and $R_1$ and $R_2$ having the meanings defined above;

and oxyethylenated phytosterols.

In a known manner, the amphiphilic lipid(s) forming the vesicles may be combined with various additives modifying the permeability or the surface charge of the vesicles. Among these additives, sterols and their derivatives and phosphoric esters of fatty alcohols may be mentioned, inter alia.

The vesicles of amphiphilic lipid(s) are generally between 10 nm and 5,000 nm in size.

The total weight of lipid(s) forming the vesicles, including, where appropriate, the additive(s) combined therewith, represents between 0.2 and 20% of the total weight of the composition, and preferably between 0.5 and 8%.

The pyrimidine derivative used according to the invention is preferably a derivative of formula:

(II)

[structure of formula II showing pyrimidine with OH, $H_2N$, $R_6$, $R_5$, N, NH groups]

in which formula:
$R_5$ represents a group $-N\begin{matrix}R_7\\R_8\end{matrix}$, in which $R_7$ and $R_8$ are selected from hydrogen and a $C_1-C_4$ alkyl, $C_2-C_5$ alkenyl, ($C_1-C_4$ alkyl)aryl and $C_4-C_7$ cycloalkyl group, or form a heterocycle with the nitrogen atom to which they are linked, selected from aziridinyl, azetidinyl, pyrrolidinyl, piperidyl, hexahydroazepinyl, heptamethylenimine, octamethylenimine, morpholine or 4-($C_1-C_4$ alkyl) piperazinyl groups, it being possible for the heterocyclic groups to be substituted on the carbon atoms with one to three $C_1-C_4$ alkyl, hydroxy or $C_1-C_4$ alkoxy groups; and $R_6$ represents hydrogen or a $C_1-C_4$ alkyl, $C_2-C_5$ alkenyl, $C_4-C_7$ cycloalkyl, aryl, ($C_1-C_4$ alkyl)aryl, aryl($C_1-C_4$ alkyl), ($C_1-C_4$ alkyl)aryl($C_1-C_4$ alkyl), alkoxy($C_1-C_4$ alkyl), ($C_1-C_4$ alkoxy)aryl($C_1-C_4$ alkyl) or haloaryl(-$C_1-C_4$ alkyl) group; and/or at least one addition salt with physiologically acceptable acids.

Preferred compounds consist of compounds of formula (II) in which $R_6$ denotes hydrogen and $R_5$ represents a group $-N\begin{matrix}R_7\\R_8\end{matrix}$, in which group $R_7$ and $R_8$ form a piperidyl ring, as well as their salts such as, for example, the sulphate. Among these compounds, the especially preferred compound consists of 6-amino-1,2-dihydro-1-hydroxy-2-imino-4-piperidinopyrimidine, generally known as minoxidil.

The pyrimidine derivative(s) may be present in the aqueous dispersion phase D in the form of a solution. It/they may also be at least partially in suspension in the aqueous phase D. In the latter case, the derivative is advantageously in the form of particles having a particle size of less than 80 microns, preferably less than 20 microns and, better still, less than 5 microns.

The pyrimidine derivative(s) is (or are) present in the composition in proportions preferably of between 0.05 and 6%, more especially between 0.10 and 5% and, better still, between 0.1 and 2%, by weight relative to the total weight of the composition.

The retinoid derivative is preferably a derivative of formula (III):

(III)

[structure of formula III showing polyene chain with A and B end groups]

in which formula:

a) either A is a group selected from the groups of formulae:

(IVa)

[cyclohexene structure]

(V)

[cyclohexenone structure with =O]

(IVb)

[cyclohexadiene structure]

(VI)

[cyclohexene structure with OH]

$$\text{(VII)}$$

B then being selected:
aa) if A is a group of formula IVa:
from the following groups:
—CHO;
—CH$_2$OR$_9$, in which R$_9$ is hydrogen or a C$_1$–C$_4$ alkyl radical;

$$-\underset{\underset{O}{\|}}{C}-R_{10},$$

where R$_{10}$ is a linear or branched C$_1$–C$_{16}$ alkyl radical;
—CH$_2$SR$_{11}$, in which R$_{11}$ is hydrogen or a methyl radical;

$$-\underset{\underset{O}{\|}}{C}-X,$$

in which X denotes:
(i) —OH;
(ii) —OR$_{12}$, where R$_{12}$ is a C$_1$–C$_{15}$ alkyl radical, an aryl(C$_1$–C$_4$ alkyl) radical substituted or unsubstituted on the aryl group, an arylcarboxy(C$_1$–C$_4$ alkyl) radical substituted or unsubstituted on the aryl group, or a hydroxy(C$_1$–C$_4$ alkyl) or amido(C$_1$–C$_4$ alkyl) radical;
(iii) —NR$_{13}$R$_{14}$, in which R$_{13}$ or R$_{14}$, which may be identical or different, denote hydrogen, a C$_1$–C$_6$ alkyl, C$_1$–C$_4$ hydroxyalkyl or substituted or unsubstituted aryl radical or a substituted or unsubstituted heterocycle, or in which R$_{13}$ and R$_{14}$, together with the nitrogen atom to which they are attached, form a substituted or unsubstituted heterocycle;
(iv) an N$_3$ group;
—CH$_2$NHR$_{15}$, where R$_{15}$ denotes a substituted or unsubstituted benzoyl radical;
ab) if A is a group of formula IVb, V, VI or VII: from —COOH and the corresponding salified or esterified forms;
b) or A is selected from the group composed of substituted or unsubstituted aryl groups, substituted or unsubstituted heterocycles, arylheterocyclic groups substituted or unsubstituted on the heterocycle or arylhomocyclic groups substituted or unsubstituted on the aromatic ring,
B then being selected from the groups —COOH and —COOR$_{16}$, where R$_{16}$ is a C$_1$–C$_4$ alkyl radical or an amide radical substituted with a C$_1$–C$_4$ alkyl; as well as their physiologically acceptable salts and esters.

The derivatives of formula (III) are preferably those in which (C$_1$–C$_4$ alkyl) denotes methyl, ethyl, n-butyl, t-butyl; (C$_1$–C$_{16}$ alkyl) denotes propyl, palmityl; aryl denotes phenyl or benzyl, the substitutents on the aryl groups being (C$_1$–C$_4$ alkyl), (C$_1$–C$_{12}$ alkoxy), hydroxyl, halogen or nitro, it being possible for the alkoxy or alkyl substituents themselves to be substituted with an OH group.

The heterocyclic groups defined in the formula (III) in section [aa)iii)] can be, inter alia, groups derived from phthalimide and from succinimide, or 4- to 6-membered heterocycles containing one or more oxygen and/or nitrogen atoms.

The derivative of the retinoid family of formula (III) defined above in section a) is, in particular, selected from retinal, retinol; retinyl acetate, propionate and palmitate; retinoic acid in all-trans, 13-cis, 9-cis, 11-cis, 9,13-dicis, 11,13-dicis forms; the corresponding zinc retinoates; the quaternary ammonium retinoates of formula:

$$R_{20}-\underset{\underset{R_{18}}{|}}{\overset{\overset{R_{17}}{|}}{N^{\oplus}}}-R_{19} \quad X^{\ominus} \qquad \text{(VIII)}$$

in which formula:
X$^{\ominus}$ denotes an all-trans- or 13-cis-retinoate radical, and
i) either R$_{17}$, R$_{18}$ and R$_{19}$, which may be identical or different, are a linear C$_1$–C$_4$ alkyl radical substituted or unsubstituted with one or more hydroxyls, R$_{20}$ being a linear C$_{12}$–C$_{18}$ alkyl or alkenyl radical;
ii) or R$_{19}$ is a group $$-(CH_2)_n-\!\!\!\!\bigcirc\!\!\!\!-R_{21}$$

in which: n is equal to 0 or 1,
R$_{21}$ represents a hydrogen or halogen atom or a hydroxyl, C$_1$–C$_{18}$ alkyl or hydroxyalkyl or C$_2$–C$_{18}$ acyl group;
R$_{17}$, R$_{18}$ and R$_{19}$ having the meanings stated under i);
iii) or R$_{17}$ and R$_{18}$ form an aliphatic heterocycle containing at least one oxygen, nitrogen or sulphur atom,
R$_{19}$ and R$_{20}$ having the meanings stated under i) and ii).

Other compounds falling within the definition of the retinoids of the formula (III) defined above in section a), and which are especially usable according to the invention, are selected from all-trans-retinoyloxyacetamide; a mixture of 2-hydroxy-1-propyl and 1-hydroxy-2-propyl all-trans-retinoates; 2-hydroxyethyl all-trans-retinoate; 4-nitrobenzyl all-trans-retinoate; benzyl all-trans-retinoate; 4-(all-trans-retinoyloxyacetyl)catechol; 2-cyclohexylethyl all-trans-retinoate; 10-carboxymethyldecyl all-trans-retinoate; 4-hydroxybutyl all-trans-retinoate; cholesteryl all-trans-retinoate; 4-bromobenzyl all-trans-retinoate; cholesteryl all-trans-retinoyloxyacetate; all-trans-retinoyloxyacetyl benzene; 4-(all-trans-retinoyloxyacetyl)bromobenzene; 4-(all-trans-retinoyloxyacetyl)nitrobenzene; 4-(all-trans-retinoyloxyacetyl)benzonitrile; all-trans-retinoyloxyacetyl-2,4-dichlorobenzene; N-(all-trans-retinoyloxy)-phthalimide; N-(all-trans-retinoyloxy)succinimide; 4-(all-trans-retinoyloxyacetyl)methoxybenzene; 4-(all-trans-retinoyloxyacetyl)phenol; 1-(all-trans-retinoyloxyacetyl)-3,4,5-trimethoxybenzene; 1-(all-trans-retinoyloxyacctyl)-2,4,6-trimethylbenzene; 4-(all-trans-retinoyloxyacetyl)toluene; 4-(all-trans-retinoyloxyacetyl)ethoxybenzene; 4-(all-trans-retinoyloxyacetyl)acetoxybenzene; 4-(all-trans-retinoyloxyacetyl)-naphthalene; 4-(all-trans-retinoyloxyacetyl)biphenyl; 4-(all-trans-retinoyloxyacetyl)-2,5-dimethoxybenzene; 1-(all-trans-retinoyloxyacetyl)-2,4-dimethylbenzene; 1-(all-trans-retinoyloxyacetyl)-3,4-diacetoxybenzene; all-trans-retinamide; 2-hydroxyethyl-all-trans-retinamide; N-ethyl-all-trans-retinamide; 4-(all-trans-retinoyl)aminophenol; N-methyldimethyldioxolane retinamide; N-(ortho-carboxyphenyl)retinamide; N-(p-carboxyphenyl)retinamide; N-hydroxypropyl-all-trans-retinamide; N-hydroxypropyl-13-cis-retinamide; N-(5-tetrazolyl)-all-trans-retinamide; N-(5-tetrazolyl)-13-cis-retinamide; N-(3,4-methylenedioxyphenylmethyl)-all-trans-retinamide; N-(n-propyl)-all-trans-retinamide; N-tert-butyl-all-trans-retinamide; N-(1,1,3,3-tetramethylbutyl)-all-trans-retinamide; N-(4-carboxymethyl-3-hydroxyphenyl)-all-trans-retinamide; N-[β-(3,4-dimethoxyphenyl)ethyl]-all-trans-retinamide; 2-(all-trans-retinoylamino)-benzotriazole; 1-(all-trans-retinoyl)-1,2,4-triazole; N-(all-trans-retinoyl)imidazole; 1-nicotinoyl-2-(all-trans-retinoyl)hydrazine; N-(all-trans-retinoyl)-morpholine; trans-β-ionone (all-trans-retinoyl)-hydrazone; N,N'-dicyclohexyl-N-(all-trans-retinoyl)-urea; acetone (all-trans-retinoyl)hydrazone; N-benzoylretinylamine; and retinoyl azide.

The groups represented by A in the formula III, and defined above in section b) in connection with the aryl, substituted aryl, heterocyclic or substituted heterocyclic groups, arylheterocyclic groups substituted on the heterocycle or arylhomocyclic groups substituted on the aromatic ring, are, in particular, selected from the following groups:

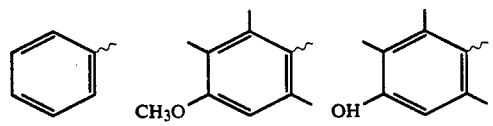

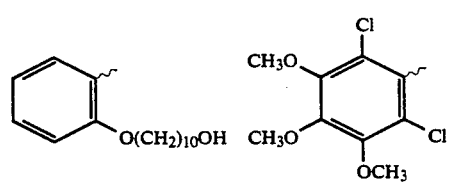

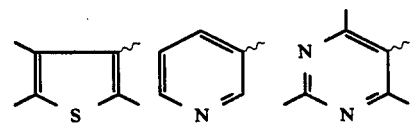

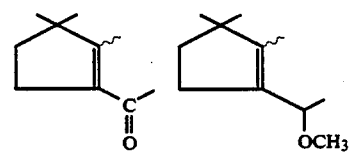

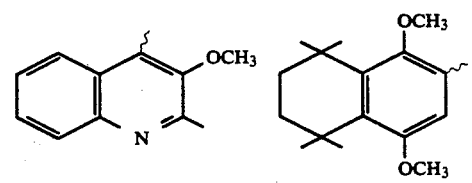

-continued

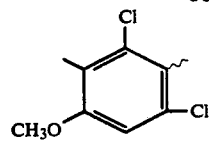

the group B then being COOH, CONHC$_2$H$_5$ or COOC$_2$H$_5$.

Especially preferred compounds in this family are motretinide and etretinate.

Other retinoids usable according to the invention are those corresponding to the following formulae (IX) to (XIV), as well as their physiologically acceptable salts or esters:

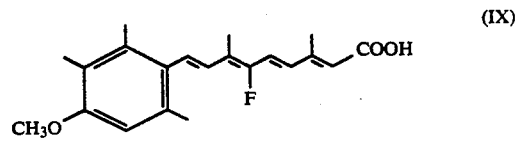
(IX)

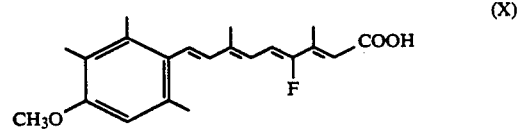
(X)

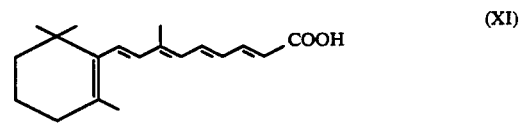
(XI)

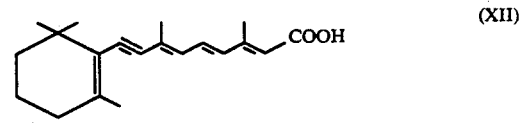
(XII)

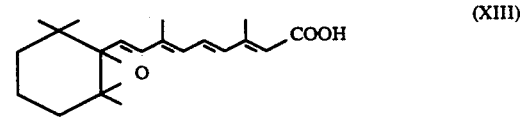
(XIII)

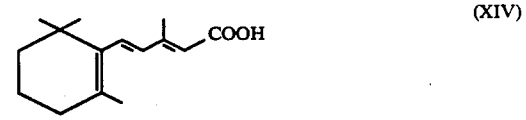
(XIV)

Compounds of the retinoid family which are usable according to the invention are also described in U.S. Pat. Nos. 4,190,594 and 4,126,698, EP-A-010,209, EP-A-010,208, EP-A-097 76, FR-A-2,293,193 and EP-A-033,095.

In the composition according to the invention, among the retinoids of formula (III) as defined in sections a) and b), preference is given more especially to those corresponding to the following general formula:

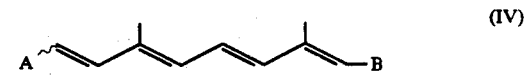
(IV)

which are in the form of all-trans or 13-cis isomers and correspond to a formula in which:
B represents:
either a group

in which V is OH; OZ, Z denoting a $C_1$-$C_{15}$ alkyl group; or an amino radical, unsubstituted or mono- or disubstituted with a $C_1$-$C_6$ alkyl;
or a —$CH_2OH$ or —CHO group; and
A represents a group

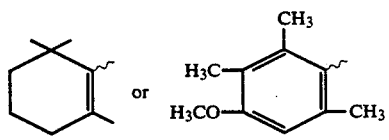

Among especially preferred derivatives, there may be mentioned the products commonly known as: isotretinoin; retinol; motretinide; etretinate; retinyl acetate, palmitate and propionate; zinc all-trans-retinoate; and still more especially tretinoin or all-trans-retinoic acid.

The composition according to the invention preferably contains minoxidil in combination with all-trans-retinoic acid.

In the composition according to the invention, the retinoid derivative of formula III in which B is —COOH is present in proportions of between 0.005% and 0.030% by weight relative to the total weight of the composition.

The aqueous phase D may be gelled. In this case, thickening or gelling agents well known in the prior art are used, such as, more especially heterobiopolysaccharides such as xanthan gum or scleroglucans, cellulose derivatives and acrylic polymers, crosslinked or otherwise.

The gelling or thickening agents are preferably present in proportions of between 0.1 and 5%, and especially between 0.4 and 3%, by weight relative to the total weight of the composition.

The aqueous phase D can also contain physiologically acceptable, water-soluble or dispersed additives. These additives are more especially those used in cosmetic or pharmaceutical compositions for topical application, such as, for example, preservatives, colourings and alkalinizing or acidifying agents.

The pH of the compositions according to the invention is preferably between 4 and 9.

The composition according to the present invention may be prepared by any known process for manufacturing vesicles of ionic or nonionic lipids, in which the retinoid derivative is introduced by adding it to the lipid mixture before performing the hydration of the said lipid mixture and forming the vesicles, and in which the pyrimidine derivative is introduced into the aqueous dispersion phase of the vesicles after formation of the vesicles.

The subject of the present invention is also the composition according to the invention for use as a medicinal product intended for inducing and stimulating hair growth and decreasing its loss.

The subject of the present invention is finally a process for treatment of the hair and scalp, characterized in that 1 to 5 g of the composition according to the invention is/are applied thereto at a frequency of one to two applications per day for 1 to 7 days per week, for a treatment period of between 1 and 6 months. The application is preferably performed on the alopecic area.

The treatment process has the features of a therapeutic treatment, inasmuch as the combination according to the invention has a therapeutic activity in respect of the biological mechanisms of the hair cycle and the dysfunctioning of the latter. This process is also a cosmetic treatment, inasmuch as it enables the hair to be made more attractive by giving it greater vitality and a more satisfactory appearance, in the absence of any particular pathological condition.

The examples given below, purely by way of illustration and without implied limitation, will permit a better understanding of the invention.

EXAMPLE 1 (Comparative)

1) Preparation of the Compositions

A composition $A_1$ corresponding to the invention, and containing 0.025% by weight, relative to the total weight of the composition, of all-trans-retinoic acid in the lipid lamellae of nonionic lipid vesicles and 0.2% by weight of minoxidil in water, was prepared according to the process described in Example 2 given below.

A composition B (not forming part of the invention), containing 0.025% by weight of all-trans-retinoic acid and 0.2% by weight of minoxidil in a solvent consisting (by volume) of 5% of propylene glycol and 95% of ethanol, was also prepared.

2) Comparative Tests

The two compositions $A_1$ and $B_1$ were stored in transparent glass bottles at variable temperatures. The concentration of all-trans-retinoic acid was measured after 15 days and the percentage of acid remaining and the loss of acid were calculated. The results obtained are given in Table I below.

TABLE I

| Temperature | Composition $A_1$ | | Composition $B_1$ | |
|---|---|---|---|---|
| | % acid remaining | loss in % | % acid remaining | loss in % |
| 4° C. | 97.4 | 2.6 | 91.7 | 8.3 |
| Room temperature | 95 | 5 | 90.7 | 9.3 |
| 45° C. | 93.3 | 6.7 | 82.3 | 17.7 |

It is seen that retinoic acid is much better preserved in a composition according to the invention than in a composition according to the prior art.

EXAMPLE 2

To prepare niosomes containing all-trans-retinoic acid in the lipid lamellae, a tank equipped with a scraping stirrer is charged at a temperature of 35° C. with the following compounds in succession:

| Nonionic lipid of formula: | |
|---|---|
| $C_{16}H_{33}$—[—$OCH_2$—CHOH—$CH_2$]$_2OH$ | 912 g |
| Cholesterol | 912 g |
| Dicetyl phosphate | 96 g |
| Methylene chloride | 10,880 g |
| all-trans-Retinoic acid (dissolved in 220 g of methylene chloride) (active substance) | 6 g |
| Ethylenediaminetetraacetic acid disodium salt | 12 g |
| Water | 23,400 g |

After the methylene chloride has been distilled off under reduced pressure (80-500×10², pascal), the temperature of the tank is raised to 52° C. and the water is distilled off under a reduced pressure of 930×10² pascal.

12 kilograms of vesicles assaying at 0.044% by weight of all-trans-retinoic acid are obtained.

The vesicles obtained are dispersed with a "Virtis" ultradisperser in an aqueous solution of minoxidil, and the following formulation A₁ is obtained:

| | |
|---|---|
| Minoxidil | 0.2 g |
| Vesicles corresponding to 0.025 g of all-trans-retinoic acid | 57 g |
| Water | qs 100 ml |

This composition was used at the rate of two topical applications of 3 g per day on the hair and scalp of a subject suffering from alopecia, every day for 3 months. A significant regrowth of the hair was noted.

EXAMPLE 3

The following formulation is prepared:

| | |
|---|---|
| Minoxidil | 1 g |
| Vesicles of Example 2 | 57 g |
| Crosslinked polyacrylic acid (MW = approximately 3 million) sold by the company "GOODRICH" under the tradename "CARBOPOL 934" | 0.5 g |
| Water | qs 100 ml |

The composition is presented in the form of a cream.

This composition was used at the rate of one topical application of 5 g per day on the hair and scalp of a subject suffering from alopecia, every day for 5 months. A significant regrowth of the hair was noted.

EXAMPLE 4

A tank equipped with a scraping stirrer is charged at a temperature of 35° C. with the following compounds in succession:

| Nonionic lipid of formula: | |
|---|---|
| $C_{16}H_{33}\text{-}[OCH_2\text{--}CHOH\text{--}CH_2]_2OH$ | 380 g |
| Cholesterol | 380 g |
| Dicetyl phosphate | 40 g |
| Methylene chloride | 3,200 g |
| all-trans-Retinoic acid | 10 g |
| Methylene chloride solubilizing the all-trans-retinoic acid | 800 g |
| DL-α-Tocopherol | 10 g |
| Ethylenediaminetetraacetic acid disodium salt | 10 g |
| Water | 13,790 g |

After the methylene chloride has been distilled off under reduced pressure, the temperature of the tank is raised to 50° C. and the water is distilled off under reduced pressure.

10 kilograms of vesicles assaying at 0.099% by weight of all-trans-retinoic acid are obtained.

The vesicles obtained are dispersed with a "VIRTIS" ultradisperser in an aqueous solution of minoxidil, and the following formulation A₂ is obtained:

| | |
|---|---|
| Minoxidil | 0.2 g |
| Vesicles corresponding to 0.025 g of all-trans-retinoic acid | 25.3 g |
| DL-α-Tocopherol | 0.025 g |
| Water | qs 100 ml |

This composition was used at the rate of one topical application of 5 g per day on the hair and scalp of a subject suffering from alopecia, every day for 5 months. A significant regrowth of the hair was noted.

A reference composition B₂ (not forming part of the invention) having the following formulation was also prepared:

| | |
|---|---|
| Minoxidil | 0.2 g |
| all-trans-Retinoic acid | 0.025 g |
| DL-α-Tocopherol | 0.025 g |
| Propylene glycol/ethyl alcohol (5:95 by volume) | qs 100 ml |

EXAMPLE 5

A tank equipped with a scraping stirrer is charged at a temperature of 35° C. with the following compounds in succession: Nonionic lipid of formula:

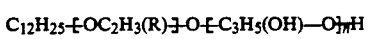

where —OC₂H₃(R)— consists of a mixture of the radicals:

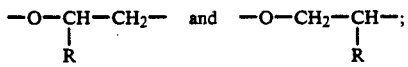

where —C₃H₅(OH)—O— consists of a mixture of the radicals:

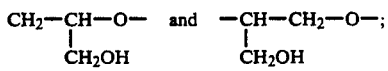

where $\bar{n}=6$;
and where R is a mixture of $C_{14}H_{29}$ and

| | |
|---|---|
| $C_{16}H_{33}$ radicals | 380 g |
| Cholesterol | 380 g |
| Methylene chloride | 3,200 g |
| all-trans-Retinoic acid | 10 g |
| Methylene chloride solubilizing the all-trans-retinoic acid | 800 g |
| DL-α-Tocopherol | 10 g |
| Ethylenediaminetetraacetic acid disodium salt | 10 g |
| Water | 13,855 g |

After the methylene chloride has been distilled off under reduced pressure, the temperature of the tank is raised to 50° C. and the water is distilled off under reduced pressure.

10 kg of vesicles assaying at 0.099% by weight of all-trans-retinoic acid are obtained.

The vesicles obtained are dispersed with a "VIRTIS" ultradisperser in an aqueous solution of minoxidil, and the following formulation A₃ is obtained:

| | |
|---|---|
| Minoxidil | 0.2 g |
| Vesicles corresponding to 0.025 g of all-trans-retinoic acid | 25.2 g |

-continued

| | |
|---|---|
| DL-α-Tocopherol | 0.025 g |
| Water | qs 100 ml |

This composition was used at the rate of one topical application of 5 g per day on the hair and scalp of a subject suffering from alopecia, every day for 5 months. A significant regrowth of the hair was noted.

A reference composition $B_3$ (not forming part of the invention), identical to the composition $B_2$ of Example 4, was also prepared.

EXAMPLE 6

A tank equipped with a scraping stirrer is charged at a temperature of 35° C. with the following compounds in succession:

| Nonionic lipid of formula: | |
|---|---|
| $C_{15}H_{31}$—CO⎡OCH$_2$—CHOH—CH$_2$⎤OH | 380 g |
| Cholesterol | 380 g |
| Dicetyl phosphate | 40 g |
| Methylene chloride | 3,280 g |
| all-trans-Retinoic acid | 10 g |
| Methylene chloride solubilizing the all-trans-retinoic acid | 800 g |
| DL-α-Tocopherol | 10 g |
| Ethylenediaminetetraacetic acid disodium salt | 10 g |
| Water | 13,800 g |

After the methylene chloride has been distilled off under reduced pressure, the temperature of the tank is raised to 50° C. and the water is distilled off under reduced pressure.

10 kg of vesicles assaying at 0.099% by weight of all-trans-retinoic acid are obtained.

The vesicles obtained are dispersed with a "VIRTIS" ultradisperser in an aqueous solution of minoxidil, and the following formulation $A_4$ is obtained:

| | |
|---|---|
| Minoxidil | 0.2 g |
| Vesicles corresponding to 0.025 g of all-trans-retinoic acid | 25.4 g |
| DL-α-Tocopherol | 0.025 g |
| Water | qs 100 ml |

This composition was used at the rate of one topical application of 5 g per day on the hair and scalp of a subject suffering from alopecia, every day for 5 months. A significant regrowth of the hair was noted.

A reference composition $B_4$ (not forming part of the invention), identical to the composition $B_2$ of Example 4, was also prepared.

EXAMPLE 7

A tank equipped with a scraping stirrer is charged at a temperature of 38° C. in two successive steps.

In a first step, the following compounds were added:

| | |
|---|---|
| Water | 10,320 g |
| Ethylenediaminetetraacetic acid disodium salt | 10 g |

In a second step, the following compounds were added:

| | |
|---|---|
| Soybean lecithin (75% phosphatidylcholine) sold by the company "SEPPIC" under the tradename "LIPOID S 75" | 600 g |
| Butylated hydroxytoluene | 7.5 g |
| DL-α-Tocopherol | 7.5 g |
| all-trans-Retinoic acid | 7.5 g |
| Methylene chloride | 2,400 g |

After the methylene chloride has been distilled off under reduced pressure, the temperature of the tank is raised to 50° C. and the water is distilled off under reduced pressure.

7.5 kg of liposomes assaying at 0.102% of all-trans-retinoic acid are obtained.

The liposomes obtained are dispersed with a "VIRTIS" ultradisperser in an aqueous solution of minoxidil, and the following formulation $A_5$ is obtained:

| | |
|---|---|
| Minoxidil | 0.2 g |
| Liposomes corresponding to 0.025 g of all-trans-retinoic acid | 25.4 g |
| DL-α-Tocopherol | 0.025 g |
| Butylated hydroxytoluene | 0.025 g |
| Water | qs 100 ml |

This composition was used at the rate of one topical application of 5 g per day on the hair and scalp of a subject suffering from alopecia, every day for 5 months. A significant regrowth of the hair was noted.

A reference composition $B_5$ (not forming part of the invention)), having the following formulation was also prepared:

| | |
|---|---|
| Minoxidil | 0.2 g |
| all-trans-Retinoic acid | 0.025 g |
| Butylated hydroxytoluene | 0.025 g |
| DL-α-Tocopherol | 0.025 g |
| Propylene glycol/ethyl alcohol (5:95 by volume) | qs 100 ml |

EXAMPLE 8

A tank equipped with a scraping stirrer is charged at a temperature of 38° C. in three successive steps.

In a first step, the following compounds were added:

| | |
|---|---|
| Water | 13,800 g |
| Ethylenediaminetetraacetic acid disodium salt | 10 g |

In a second step, the following compounds were added:

| | |
|---|---|
| Hydrogenated lecithin containing 30/35% of hydrogenated phosphatidylcholine, sold by the company "NIKKO" under the name "LECINOL S 10" | 480 g |
| Polyoxyethylenated phytosterol (containing 5 moles of ethylene oxide) sold by the company "NIKKO" under the name "GENEROL 122 E 5" | 320 g |
| Methylene chloride (solubilizing the "LECINOL" and the "GENEROL") | 3,200 g |

In a third step, the following compounds were added:

| | |
|---|---|
| all-trans-Retinoic acid | 10 g |
| DL-α-Tocopherol | 10 g |
| Methylene chloride (solubilizing the DL-α-tocopherol) | 800 g |

After the methylene chloride has been distilled off under reduced pressure, the temperature of the tank is raised to 50° C. and the water is distilled off under reduced pressure.

10 kg of liposomes assaying at 0.05% by weight of all-trans-retinoic acid are obtained.

The vesicles obtained are dispersed with a "VIRTIS" ultradisperser in an aqueous solution of minoxidil, and the following formulation $A_6$ is obtained:

| | |
|---|---|
| Minoxidil | 0.2 g |
| Liposomes corresponding to 0.025 g of all-trans-retinoic acid | 50 g |
| DL-α-Tocopherol | 0.05 g |
| Water | qs 100 ml |

This composition was used at the rate of one topical application of 5 g per day on the hair and scalp of a subject suffering from alopecia, every day for 5 months. A significant regrowth of the hair was noted.

The reference composition $B_6$ (not forming part of the invention), having the following formulation was also prepared:

| | |
|---|---|
| Minoxidil | 0.2 g |
| all-trans-Retinoic acid | 0.025 g |
| DL-α-Tocopherol | 0.05 g |
| Propylene glycol/ethyl alcohol (5:95 by volume) | qs 100 ml |

EXAMPLE 9 (Comparative)

The compositions $A_2$ to $A_6$ and the corresponding reference compositions $B_2$ to $B_6$ were exposed to daylight in transparent glass bottles.

The daylight-induced photodegradation of all-trans-retinoic acid in the presence of minoxidil in these compositions was assessed by measuring the concentration of all-trans-retinoic acid at specified time intervals. The concentrations of all-trans-retinoic acid, in % relative to the initial concentration, are given in Table II below for the different compositions and for different irradiation times.

TABLE II

| Composition | Irradiation time in minutes | | | | |
|---|---|---|---|---|---|
| | 0 | 20 | 40 | 80 | 120 |
| $A_2$ | 100 | 69 | 44 | 43 | 43 |
| $A_3$ | 100 | 71 | 59.5 | 49 | 42 |
| $A_4$ | 100 | 75 | 52 | 46.5 | 41 |
| $B_2 = B_3 = B$ | 100 | 46 | 27.5 | 19 | 18 |
| $A_5$ | 100 | 62 | 54 | 35.5 | 27.5 |
| $A_6$ | 100 | 70 | 49 | 37 | 32 |
| $B_5$ | 100 | 45.5 | 35 | 20 | 17.5 |
| $B_6$ | 100 | 47.5 | 37.5 | 22.5 | 19 |

It may be seen in Table II that, in the compositions according to the invention, the all-trans-retinoic acid decomposes much less rapidly than in the compositions of the prior art. For example, after 120 minutes' exposure to daylight, the compositions according to the invention $A_2$ to $A_4$ contain more than 40% of all-trans-retinoic acid, whereas the compositions of the prior art $B_2$ to $B_4$ contain less than 20% of all-trans-retinoic acid, that is to say less than half as much.

We claim:

1. Cosmetic or pharmaceutical composition for topical application containing, in combination, at least one retinoid derivative and at least one pyrimidine derivative, characterized in that it consists of a dispersion of vesicles of at least one ionic and/or nonionic amphiphilic lipid, the vesicles being bounded by one or more lipid lamella(e) in a physiologically acceptable aqueous dispersion phase D, the retinoid derivative(s) being in the lipid lamellae of the vesicles whereas the pyrimidine derivative(s) is (or are) in the form of a solution or, partially or totally, in the form of a suspension in the aqueous phase D.

2. Composition according to claim 1, characterized in that the amphiphilic lipid(s) forming the lamellae of the vesicles is (or are) one (or more) ionic lipid(s) selected from the group composed of natural or synthetic phospholipids.

3. Composition according to claim 1, characterized in that the amphiphilic lipid(s) forming the lamellae of the vesicles is (or are) one (or more) nonionic lipid(s) selected from the group composed of the compounds of formula (I):

$$RO\text{-}[C_3H_5(OH)O]_{\overline{n}}OH \quad (I)$$

where $-C_3H_5(OH)$ $O-$ is represented by the following structures, taken mixed or separately:

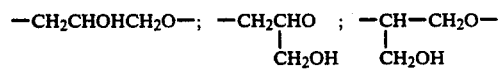

where $\overline{n}$ is an average statistical value between 2 and 6; where R is:

a) either an aliphatic chain $R_1$ or a residue $R_2CO$, $R_1$ being a linear or branched $C_{12}$-$C_{18}$ aliphatic radical and $R_2$ being a linear or branched $C_{11}$-$C_{17}$ aliphatic radical;

b) or $R_3\text{-}[O\text{-}C_2H_3(R_4)]\text{-}$
where $-OCH_2H_3(R_4)-$ is represented by the following structures, taken mixed or separately:

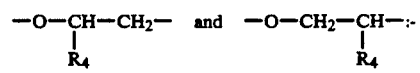

$R_3$ being a radical $R_1$ or $R_2CO$, $R_4$ being a radical $R_1$, and $R_1$ and $R_2$ having the meanings defined above; and oxyethylenated phytosterols.

4. Composition according to claim 1, characterized in that the amphiphilic lipid(s) of the lamellae is (or are) combined with at least one additive modifying the permeability or the surface charge of the vesicles.

5. Composition according to claim 1, characterized in that the total weight of lipid(s) forming the vesicles, including, where appropriate, the additive(s) combined therewith, represents between 0.2 and 20% of the total weight of the composition.

6. Composition according to claim 1, characterized in that it contains at least one pyrimidine derivative of the formula:

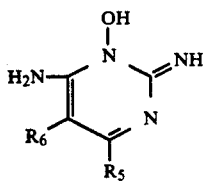
(II)

in which formula:
$R_5$ represents a group

in which $R_7$ and $R_8$ are selected from hydrogen and a $C_1$–$C_4$ alkyl, $C_2$–$C_5$ alkenyl, ($C_1$–$C_4$ alkyl)aryl and $C_4$–$C_7$ cycloalkyl group, or form a heterocycle with the nitrogen atom to which they are linked, selected from aziridinyl, azetidinyl, pyrrolidinyl, piperidyl, hexahydroazepinyl, heptamethylenimine, octamethylenimine, morpholine or 4-($C_1$–$C_4$ alkyl) piperazinyl groups, it being possible for the heterocyclic groups to be substituted on the carbon atoms with one to three $C_1$–$C_4$ alkyl, hydroxy or $C_1$–$C_4$ alkoxy groups; and $R_6$ represents hydrogen or a $C_1$–$C_4$ alkyl, $C_2$–$C_5$ alkenyl, $C_4$–$C_7$ cycloalkyl, aryl, ($C_1$–$C_4$ alkyl)aryl, aryl(-$C_1$–$C_4$ alkyl), ($C_1$–$C_4$ alkyl)aryl($C_1$–$C_4$ alkyl), alkoxy($C_1$–$C_4$ alkyl), ($C_1$–$C_4$ alkoxy)aryl($C_1$–$C_4$ alkyl) or haloaryl($C_1$–$C_4$ alkyl) group; and/or at least one addition salt with physiologically acceptable acids.

7. Composition according to claim 6, characterized in that it contains 6-amino-1,2-dihydro-1-hydroxy-2-imino-4-piperidinopyrimidine and/or at least one of its physiologically acceptable addition salts.

8. Composition according to claim 1, characterized in that it contains at least one pyrimidine derivative which is at least partially in the form of a suspension, in the aqueous phase D, of particles having a particle size of less than 80 microns.

9. Composition according to claim 1, characterized in that the pyrimidine derivative(s) is (or are) present in the composition in proportions of between 0.05 and 6% by weight relative to the total weight of the composition.

10. Composition according to claim 1, characterized in that the retinoid derivative is a derivative of formula (III):

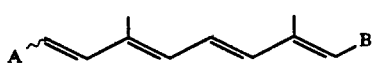
(III)

in which formula:
a) either A is a group selected from the groups of formulae:

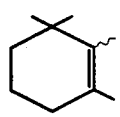
(IVa)

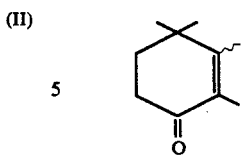
(V)

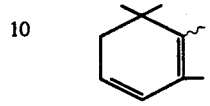
(IVb)

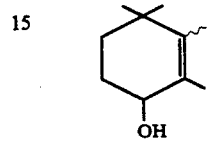
(VI)

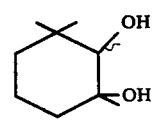
(VII)

B then being selected:
aa) if A is a group of formula IVa:
from the following groups:
—CHO;
—$CH_2OR_9$, in which $R_9$ is hydrogen or a $C_1$–$C_4$ alkyl radical;

$$-\underset{\underset{O}{\|}}{C}-R_{10},$$

where $R_{10}$ is a linear or branched $C_1$–$C_{16}$ alkyl radical;
—$CH_2SR_{11}$, in which $R_{11}$ is hydrogen or a methyl radical;

$$-\underset{\underset{O}{\|}}{C}-X,$$

in which X denotes:
(i) —OH;
(ii) —$OR_{12}$, where $R_{12}$ is a $C_1$–$C_{15}$ alkyl radical, an aryl($C_1$–$C_4$ alkyl) radical substituted or unsubstituted on the aryl group, an arylcarboxy($C_1$–$C_4$ alkyl) radical substituted or unsubstituted on the aryl group, or a hydroxy($C_1$–$C_4$ alkyl) or amido($C_1$–$C_4$ alkyl) radical;
(iii) —$NR_{13}R_{14}$, in which $R_{13}$ or $R_{14}$, which may be identical or different, denote hydrogen, a $C_1$–$C_6$ alkyl, $C_1$–$C_4$ hydroxyalkyl or substituted or unsubstituted aryl radical or a substituted or unsubstituted heterocycle, or in which $R_{13}$ and $R_{14}$, together with the nitrogen atom to which they are attached, form a substituted or unsubstituted heterocycle;
(iv) an $N_3$ group;
—$CH_2NHR_{15}$, where $R_{15}$ denotes a substituted or unsubstituted benzoyl radical;
ab) if A is a group of formula IVb, V, VI or VII: from —COOH and the corresponding salified or esterified forms;

b) or A is selected from the group composed of substituted or unsubstituted aryl groups, substituted or unsubstituted heterocycles, arylheterocyclic groups substituted or unsubstituted on the heterocycle or arylhomocyclic groups substituted or unsubstituted on the aromatic ring, B then being selected from the groups —COOH and —COOR$_{16}$, where R$_{16}$ is a C$_1$–C$_4$ alkyl radical or an amide radical substituted with a C$_1$–C$_4$ alkyl; as well as their physiologically acceptable salts and esters.

11. Composition according to claim 10, characterized in that the retinoid derivative is a derivative of formula (III) for which (C$_1$–C$_4$ alkyl) denotes methyl, ethyl, n-butyl, t-butyl; (C$_1$–C$_{16}$ alkyl) denotes ethyl, propyl, palmityl; aryl denotes phenyl or benzyl, the substituents on the aryl groups being (C$_1$–C$_4$ alkyl), (C$_1$–C$_{12}$ alkoxy), hydroxyl, halogen or nitro, it being possible for the alkoxy or alkyl substituents themselves to be substituted with an OH group.

12. Composition according to claim 10, characterized in that the retinoid derivative is a derivative of formula (III) containing a heterocyclic group selected from the group composed of groups derived from phthalimide and from succinimide and 4- to 6-membered heterocycles containing one or more oxygen atoms and/or one or more nitrogen atoms.

13. Composition according to claim 10, characterized in that the retinoid derivative is selected from the group composed of retinal; retinol; retinyl acetate, propionate and palmitate; retinoic acid in all-trans, 13-cis, 9-cis, 11-cis, 9,13-dicis, 11,13-dicis forms; the corresponding zinc retinoates; motretinide; etretinate; the quaternary ammonium retinoates of formula:

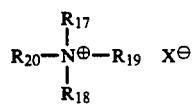

(VIII)

in which formula:

X$^\ominus$ denotes an all-trans- or 13-cis-retinoate radical, and i) either R$_{17}$, R$_{18}$ and R$_{19}$, which may be identical or different, are a linear C$_1$–C$_4$ alkyl radical substituted or unsubstituted with one or more hydroxyls, R$_{20}$ being a linear C$_{12}$–C$_{18}$ alkyl or alkenyl radical;

ii) or R$_{19}$ is a group

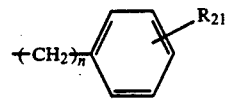

in which: n is equal to 0 or 1,

R$_{21}$ represents a hydrogen or halogen atom or a hydroxyl, C$_1$–C$_{18}$ alkyl or hydroxyalkyl or C$_2$–C$_{18}$ acyl radical;

R$_{17}$, R$_{18}$ and R$_{19}$ having the meanings stated under i);

iii) or R$_{17}$ and R$_{18}$ form an aliphatic heterocycle containing at least one oxygen, nitrogen or sulphur atom, R$_{19}$ and R$_{20}$ having the meanings stated under i) and ii).

14. Composition according to claim 1, characterized in that it contains minoxidil as a pyrimidine derivative, and all-trans-retinoic acid as a retinoid derivative.

15. Composition according to claim 1, characterized in that the retinoid derivative of formula (III) in which B is —COOH is present in proportions of between 0.005% and 0.030% by weight relative to the total weight of the composition.

16. Composition according to claim 1, characterized in that the aqueous phase D is gelled.

17. Composition according to claim 16, characterized in that the gelling agent is selected from the group composed of heterobiopolysaccharides, cellulose derivatives and acrylic polymers, crosslinked or otherwise.

18. Composition according to claim 16, characterized in that the gelling agent is present in a proportion of between 0.1 and 5% by weight relative to the total weight of the composition.

19. Composition according to claim 1, characterized in that the aqueous phase D contains at least one physiologically acceptable, water-soluble additive.

20. Composition according to claim 1, characterized in that its pH is between 4 and 9.

21. Process for cosmetic treatment of the hair and scalp, characterized in that 1 to 5 g of the composition according to claim 1 is applied thereto by massage at a frequency of one to two applications per day for 1 to 7 days per week, for a treatment period of between 1 and 6 months.

* * * * *